United States Patent
Meyer et al.

(10) Patent No.: US 6,958,418 B2
(45) Date of Patent: Oct. 25, 2005

(54) PROCESS FOR PREPARING VANILLYLAMINE HYDROCHLORIDE

(75) Inventors: Oliver Meyer, Dorsheim (DE); Ingo Heddesheimer, Monzingen (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/864,263

(22) Filed: Jun. 9, 2005

(65) Prior Publication Data

US 2004/0225155 A1 Nov. 11, 2004

Related U.S. Application Data

(63) Continuation of application No. 10/259,120, filed on Sep. 27, 2002, now abandoned.
(60) Provisional application No. 60/334,696, filed on Nov. 20, 2001.

(30) Foreign Application Priority Data

Sep. 28, 2001 (DE) .......................................... 101 47 958

(51) Int. Cl.$^7$ ............................................. C07C 211/27
(52) U.S. Cl. ........................ 564/336; 564/259; 514/654
(58) Field of Search ................................ 564/259, 336, 564/654; 514/654

(56) References Cited

U.S. PATENT DOCUMENTS 2,711,428 A   6/1955   Goodson et al.

OTHER PUBLICATIONS

Gannett et al., "The Capsaicinoids: Their Separation, Synthesis, and Mutagenicity," J. Org. Chem., 1988, 53, 1064–1071, pp. 1064–1071.*
Preuner, R.; Chem. Abstract 46:21302 (1952).
March, Jerry; Advanced Organic Chemistry: Reactions, Mechanisms, and Structure: Reactions vol. 6 No. 23 p. 675; McGraw–Hill Book Co. New York (1968).

* cited by examiner

*Primary Examiner*—Peter O'Sullivan
(74) *Attorney, Agent, or Firm*—Michael P. Morris; Mary-Ellen M. Devlin; Alan R. Stempel

(57) ABSTRACT

Process for preparing vanillylamine or one of the salts thereof by reacting vanillin with hydroxylamine or the salts thereof in the presence of an organic salt, which may optionally be produced in situ, wherein the reaction is carried out in an inorganic or organic acid as diluent, and subsequently hydrogenating the resulting vanillyloxime with hydrogen in the presence of a suitable catalyst and an organic and/or inorganic acid.

8 Claims, No Drawings

PROCESS FOR PREPARING VANILLYLAMINE HYDROCHLORIDE

RELATED APPLICATIONS

This application is a continuation of U.S. patent application Ser. No. 10/259,120, filed Sep. 27, 2002 and U.S. Provisional Application Ser. No. 60/334,696, filed Nov. 20, 2001, both of which are incorporated by reference herein in their entireties.

BACKGROUND TO THE INVENTION

The invention relates to a process for preparing vanillylamine hydrochloride which can be used on an industrial scale.

Vanillylamine hydrochloride is an intermediate product in the preparation of pelargonic acid vanillylamide, which is used as a hyperemia inducing active substance, e.g. in plasters.

German Patent DE 760 746 describes the preparation of vanillylamine hydrochloride, in which the isolated 4-hydroxy-3-methoxy-benzaldoxime used as starting material is reduced using hydrogen in the presence of activated charcoal and palladium oxide in an acetic acid solution and with the subsequent addition of hydrochloric acid to obtain the vanillylamine hydrochloride.

The preparation of 4-hydroxy-3-methoxy-benzaldoxime from vanillin and hydroxylamine hydrochloride in a basic medium is described in the literature (Ganett, P. M., J. Org. Chem. Vol. 53, No. 5, 1988). First, the oxime is isolated and then reduced to the amine in an ethanolic hydrochloric acid solution. The isolation of the oxime represents a significant expenditure of cost and time, particularly in the production of vanillylamine hydrochloride on an industrial scale.

The problem overcome by the present invention is therefore to prepare a cost effective process for preparing vanillylamine hydrochloride which can be used on an industrial scale.

DETAILED DESCRIPTION OF THE INVENTION

The present invention solves the problem described above by the following method of synthesis.

The invention thus relates to a process for preparing vanillylamine or one of the salts thereof by:

a) reacting vanillin with hydroxylamine or the salts thereof in the presence of an organic salt, which may optionally be produced in situ; and b) subsequently hydrogenating the resulting vanillyloxime with hydrogen in the presence of a suitable catalyst and an organic and/or inorganic acid, wherein step a) is carried out in an inorganic or organic acid as diluent.

In a preferred process, steps a) and b) are carried out in a one-pot process.

Also preferred is a process wherein step a) is carried out in the presence of sodium acetate and glacial acetic acid.

In a particularly preferred process vanillin is reacted with hydroxylamine hydrochloride in step a).

Also particularly preferred is a process wherein Pd/C or Pt/C is used as catalyst in step b).

Of particular importance according to the invention is a process wherein the hydrogenation step b) is carried out in the presence of glacial acetic acid and concentrated hydrochloric acid.

The invention preferably relates to a process wherein the reaction temperature in step a) is 15° C. to 50° C.

The invention preferably relates to a process wherein the reaction temperature in step b) is 0° C. to 70 C.

Particularly preferred is a process wherein vanillin is used in a molar ratio to hydroxylamine or the salt thereof of 1:2 to 2:1, preferably 1:1.

The invention also relates to the use of the vanillylamine or one of the salts thereof obtained by the process according to the invention for preparing pharmaceutically active compounds.

The invention further relates to the use of the vanillylamine or one of the salts thereof obtained by the process according to the invention for preparing pelargonic acid vanillylamide.

Acids suitable for forming salts of vanillylamine or vanillyloxime include, for example, hydrochloric acid, acetic acid, hydrobromic acid, sulphuric acid, phosphoric acid, nitric acid, succinic acid, oxalic acid, malonic acid, fumaric acid, maleic acid, tartaric acid, citric acid, ascorbic acid and methanesulphonic acid, particularly hydrochloric acid, sulphuric acid or acetic acid.

In a preferred embodiment of the process according to the invention for preparing the vanillylamine, as a rule one equivalent of vanillin is suspended in 3 to 20 parts (based on the weight of vanillin used), preferably about 5 parts, of an acid diluent, preferably glacial acetic acid, hydrochloric acid or sulphuric acid, most preferably glacial acetic acid, and combined with 1 to 2 equivalents, preferably one equivalent of an organic salt, for example sodium hydroxide or sodium acetate, preferably sodium acetate, most preferably anhydrous sodium acetate.

The suspension is combined with 1 to 2 equivalents, preferably one equivalent, of hydroxylamine or a hydroxylamine salt, preferably hydroxylamine hydrochloride or hydroxylamine sulphate, preferably hydroxylamine hydrochloride, with stirring. The reaction mixture is heated to 25° C. to 50° C., preferably 28° C. to 40° C., more preferably about 30° C. to 35° C., and stirred for 0.5 to 8 hours, preferably about 3 hours. The vanillyloxime produced remains in suspension and is hydrogenated by the addition of 0.1 to 10 parts (based on the weight of vanillin used), preferably about 0.7 parts, of acid, preferably hydrochloric acid or sulphuric acid, more preferably hydrochloric acid, and 1 to 20% by weight (based on the vanillin used), preferably 10% by weight, of a catalyst, preferably a transition metal catalyst, preferably a Pd/C, Pt or Ra—Ni catalyst, most preferably a Pd/C catalyst, while hydrogen is piped into the reaction mixture, under a hydrogen pressure of 1 to 7 bar, but preferably from 3 to 5 bar, most preferably 4 bar, at a temperature of 0° C. to 70° C., preferably 10° C. to 35° C., preferably about 10° C.

Then the vanillylamine produced or the salt thereof is completely dissolved by the addition of water and optionally heating to 40° C. to 70° C., preferably about 60° C. The catalyst is filtered off. The filtrate is heated to 50° C. to 70° C., preferably about 60° C., optionally after the diluent used, preferably acetic acid, has been distilled off, in order to dissolve the salts and the vanillylamine or the salt thereof, and water is added thereto. In order to precipitate the vanillylamine salt the reaction mixture is combined with an inorganic or organic acid, preferably hydrochloric acid. The suspension formed is cooled and the salt of the vanillylamine is filtered, optionally washed with a solvent, preferably acetone, and dried.

The procedure according to the invention results in a cost effective process with a high space/time yield with regard to the vanillylamine or the salts thereof.

The Examples that follow serve to illustrate some processes for preparing vanillylamine or the salts thereof which are carried out by way of example. They should be understood as being only possible procedures described purely by way of example without restricting the invention to their content.

Indeed, various modifications of the invention, in addition to those shown and described herein will become apparent to those skilled in the art from the foregoing description and accompanying drawings. Such modifications are intended to fall within the scope of the appended claims.

Various patent applications and publications are cited herein, the disclosures of which are incorporated by reference in their entireties.

EXAMPLE 1 a) Synthesis of Vanillyloxime 56.58 g of vanillin are suspended in 283 ml of glacial acetic acid and combined with 32.02 g of anhydrous sodium acetate. Then, 28.29 g of hydroxylamine hydrochloride are added, the reaction mixture is heated to 30° C. to 35° C. with stirring and stirred for 30 hours.

b) Synthesis of Vanillylamine

The reaction mixture obtained in a) is combined with 38 ml of hydrochloric acid and 6.2 g of Pd/C. Hydrogen is piped into the reaction mixture, with stirring, at 10° C. over a period of 4 hours under a pressure of 4 bar. After the addition of 71 ml of water the mixture is heated to 60° C. and stirred for 1 hour. The catalyst is filtered off and the acetic acid is eliminated from the filtrate by distillation at 60° C. Then the reaction mixture is combined with 141 ml of water in order to dissolve the vanillylamine hydrochloride and the salts and stirred at 60° C. for 0.5 hours. After the addition of 99 ml of hydrochloric acid and stirring for 1 hour, the suspension formed is cooled to 3° C. and after 3 hours the vanillylamine hydrochloride is filtered off, washed with acetone and dried at 50° C.

Yield: 57.66 g (82% of theory).

EXAMPLE 2 a) Synthesis of Vanillyloxime 20.0 g of vanillin are suspended in 150 ml of glacial acetic acid and combined with 8.6 ml of NaOH (50%). Then 10.96 g of hydroxylamine hydrochloride are added. The reaction mixture is stirred for 2 hours at 20° C.

b) Synthesis of Vanillylamine Hydrochloride

The reaction mixture obtained in a) is combined with 27 ml of hydrochloric acid and 2 g of Pd/C. Hydrogen is piped into the reaction mixture, with stirring, at 0° C. over a period of 2.5 hours under a pressure of 4 bar. After working up, 13.12 g (53% of theory) of vanillylamine hydrochloride are obtained.

What is claimed is:

1. A process for preparing vanillylamine or a salt thereof comprising:
    a. reacting vanillin with hydroxylamine or the salt thereof in the presence of an organic salt; and
    b. hydrogenating the resulting vanillyloxime with hydrogen in the presence of a suitable catalyst and an organic acid or inorganic acid or a combination of an organic and inorganic acid;
   wherein step (a) is carried out in an inorganic or organic acid as diluent; and further wherein steps (a) and (b) are carried out in a single, reaction vessel.

2. The process according to claim 1, wherein sodium acetate and glacial acetic acid are used in step (a).

3. The process according to claim 1 wherein vanillin is reacted with hydroxylamine hydrochloride in step (a).

4. The process according to claim 1 wherein Pd/C or Pt/C is used as catalyst in step (b).

5. The process according to claim 1 wherein the hydrogenation in step (b) is carried out in the presence of glacial acetic acid and concentrated hydrochloric acid.

6. The process according to claim 1 wherein the reaction temperature in step (a) is 15° C. to 50° C.

7. The process according to claim 1 wherein the reaction temperature in step (b) is 0° C. to 70° C.

8. The process according to claim 1 wherein the vanillin is used in a molar ratio to hydroxylamine or a salt thereof of 1:2 to 2:1.

* * * * *